United States Patent
Neuberger et al.

(10) Patent No.: US 8,827,991 B2
(45) Date of Patent: Sep. 9, 2014

(54) MEDICAL LASER TREATMENT DEVICE AND METHOD UTILIZING TOTAL REFLECTION INDUCED BY RADIATION

(75) Inventors: Wolfgang Neuberger, Dubai (AE); Walter Cecchetti, Saonara (IT)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 467 days.

(21) Appl. No.: 12/756,010

(22) Filed: Apr. 7, 2010

(65) Prior Publication Data
US 2010/0262131 A1    Oct. 14, 2010

Related U.S. Application Data

(60) Provisional application No. 61/168,099, filed on Apr. 9, 2009.

(51) Int. Cl.
*A61B 18/18* (2006.01)
(52) U.S. Cl.
USPC .......................................................... 606/16
(58) Field of Classification Search
USPC .......................... 606/16, 14; 372/6; 29/426.2
See application file for complete search history.

(56) References Cited

U.S. PATENT DOCUMENTS

| | | | | |
|---|---|---|---|---|
| 2006/0285798 | A1* | 12/2006 | Brekke et al. | 385/47 |
| 2007/0106286 | A1* | 5/2007 | Harschack et al. | 606/17 |
| 2009/0287198 | A1* | 11/2009 | Hanley et al. | 606/15 |

* cited by examiner

*Primary Examiner* — Tuan Nguyen
(74) *Attorney, Agent, or Firm* — Bolesh J. Skutnik; B J Associates

(57) ABSTRACT

A device for improved surgical procedures to remove unwanted or hyperplasic tissue from a patient during laser ablation, urological treatments, benign prostatic hyperplasia treatments and other applications. Specially prepared optical waveguide tips allow for enhanced irradiation of desired tissues with light sources including laser diodes, bright LEDs or lamps. A significant fraction of the optical radiation, being transported in the waveguide, is coupled out of the waveguide into the surrounding medium through a peripheral surface at or near the distal end. The optical radiation is chosen to have an appropriate wavelength and sufficient power density, so that the surrounding medium will be changed in the vicinity of at least a part of the peripheral surface area. The changes of the surrounding medium result in a change of its refractive index such that the optical radiation is redirected.

21 Claims, 4 Drawing Sheets

MEDICAL LASER TREATMENT DEVICE AND METHOD UTILIZING TOTAL REFLECTION INDUCED BY RADIATION

DOMESTIC PRIORITY UNDER 35 USC 119(e)

This application claims the benefit and priority of U.S. Provisional Application Ser. No. 61/168,099 filed Apr. 9, 2009, entitled "Medical laser treatment device and method utilizing total reflection induced by radiation" by Wolfgang Neuberger and Walter Cecchetti, which is incorporated by reference herein.

BACKGROUND OF THE INVENTION

1. Field of the Invention

The present invention relates to laser systems for medical treatments and in particular, for laser surgical procedures. More particularly, it relates to optical fiber systems and methods used for surgical treatment of various medical conditions, including benign prostatic hyperplasia (BPH).

2. Invention Disclosure Statement

Numerous medical applications (e.g. endoluminar treatment of varicose veins, laser treatment of BPH or of hemorrhoids) require the treatment of a target tissue area that is not directly in front of the fiber but located sideways. As many of those therapies have to be performed intra-corporal in an environment providing only reduced space, the direct positioning and pointing of the fiber tip of a so-called bare fiber is not applicable.

Fiber optical probes with tailored emission characteristics (e.g. side firing fibers) are feasible for those treatment procedures and turned out to be advantageous. Many attempts to use reflection effect to direct light laterally have been proposed.

Among the earliest, Abe et al teaches in U.S. Pat. No. 4,740,047 a side fiber constructed such that a transparent tubular member is coupled to the forward end portion of a fiber through two coating layers, and an anti-reflection coating layer is formed on a laser beam exiting surface of the transparent tubular member. The clad-core dimensions of examples were about 1.5 to 1. Also, U.S. Pat. No. 5,292,320 by Brown et al discloses an optical fiber, having a core and a cladding wherein the cladding has a refractive index smaller than the core, having an input end suitably configured to connect to an appropriate radiation source and having a distal end in the proximity of which two or more grooves are penetrating into the core. The grooves have at least partial reflector capability so as to deflect radiation thereto radially in one or more predetermined patterns. In one embodiment this invention has a fused proximal end of cover tube over distal end cladding of the fiber to create an air gap over structured distal tip. Another example of recent prior art in side fibers can be appreciated in U.S. Pat. No. 5,509,917 by Cecchetti et al. A side fiber is presented wherein laser beam in the optical fiber is totally reflected down toward the side of the fiber using an obliquely cut tip due to the refractive index differences between the fiber core and that of the air gap formed in the cap, and with the cap in the path of radiation transmission can be fused to the clad fiber at the distal end to reduce/eliminate Fresnel loss as the side firing fiber transmits the laser energy. Another example is found in U.S. Patent Application No. 2007/0106286 by Harschack et al. which propose a side fire optical fiber tip for high power applications. A predetermined length of an output tip on the distal end of the optical fiber is formed with an optical fiber core and cladding layer of preselected thickness wherein the cladding to core diameter ratio is 1.2. Over optical fiber output end, a silica capillary tube is fused to the exposed cladding. These types of fiber probes direct the optical radiation into the desired direction as they take advantage of the effect of total reflection at a boundary layer with a feasible refractive index step, i.e. where the refractive index on the other side of said boundary layer is significantly lower than inside the glass optical fiber. Mostly, the fiber tip is encapsulated in a sealed cap together with a small volume of air. The enclosed air provides the necessary refractive index step which allows for the redirection of the optical radiation guided by the glass optical fiber. Furthermore, the end cap protects the structured fiber end tip from environmental influences and thus e.g. prevents it from mechanical damage and protects the patient from injuries.

Hanley et al in US Application Publication 2009/0287198 A1, presents an apparatus that includes a distal of an optical fiber core having a multilayer dielectric coating, disposed on an angled surface at the core distal end to produce internal reflection of laser energy at the angled surface, the coating and angled surface collectively configured to redirect laser energy in a lateral direction. Brekke et. al, in U.S. Pat. No. 7,463,801 proposes a side fiber having both a core and a cladding surrounding the core. The optical fiber terminates at a distal tip having a surface inclined relative to the axis of the fiber. A tubular member surrounds the optical fiber at its distal end. The distal end of the optical fiber has a portion opposing the tubular member for being united to the tubular member. The distal portion is joined to the tubular member by an intermediate material selected to have an index of refraction matching that of the core and the tubular member. U.S. Pat. No. 5,366,456 by Rink et. al discloses a device with a firing tip which has an insert with a highly polished mirrored surface lying at a specific angle with respect to the longitudinal axis of the optical fiber. Thus, impinging laser radiation is reflected to the side and delivered at a right angle to the fiber.

As can be appreciated, once again, these are complex configurations that try to achieve appropriate refraction index difference combinations between different materials to reflect radiation in the desired direction. The end cap is glued and/or fused to the glass optical fiber. Thus, the distal endings of those fiber probes are often bulky and difficult to produce. Furthermore, the bonding of end cap and glass optical fiber might suffer from a reduced damage threshold, especially in those cases where fiber and cap are glued and the treatment requires high optical energy. Additionally many of these inventions require a relatively large probe diameter. Many minimal invasive treatment procedures require the delivery of the glass optical fiber through an endoscope. Therefore, the maximum outer diameter of a medical probe is limited by the inner diameter of the endoscope's channel. Typically, this inner diameter is of the order of 2 mm.

There is thus, a need to provide such instruments and methods as further described by the present invention.

OBJECTIVES AND SUMMARY OF THE INVENTION

It is an objective of the present invention to provide a device and method for improved surgical procedures, such as urological treatments, and tissue ablation.

It is another objective of the present invention to more easily treat benign prostatic hyperplasia by means of high power vaporization of prostatic tissue as well as lobe excavation.

It is yet another objective of the present invention to provide a surgical device and method for the removal of tumorous or hyperplasic tissue or other unwanted tissue in the body in an improved, efficient manner.

Briefly stated, a device and method are provided for improved surgical procedures to remove unwanted or hyperplasic tissue from a patient. In particular, laser ablation, urological treatments, benign prostatic hyperplasia treatments and other applications benefit from the device and method. Specially prepared optical waveguide tips allow for enhanced irradiation of desired tissues with light sources including laser diodes, bright LEDs or lamps. The refractive indices of the waveguide materials and the surrounding medium are such that a significant fraction of the optical radiation, being transported in the waveguide, is coupled out of the waveguide into the surrounding medium through a peripheral surface at or near the distal end. The optical radiation is chosen to have an appropriate wavelength and sufficient power density, so that the surrounding medium will be changed in the vicinity of at least a part of the peripheral surface area. The changes of the surrounding medium result in a change of its refractive index such that the optical radiation is redirected. Device is particularly useful for treatments within a patient where entry and/or treatment space is limited/restricted.

The above and other objects, features and advantages of the present invention will become apparent from the following description read in conjunction with the accompanying drawings (in which like reference numbers in different drawings designate the same or similar elements).

DETAILED DESCRIPTION OF THE PREFERRED EMBODIMENTS

Figure 1A:
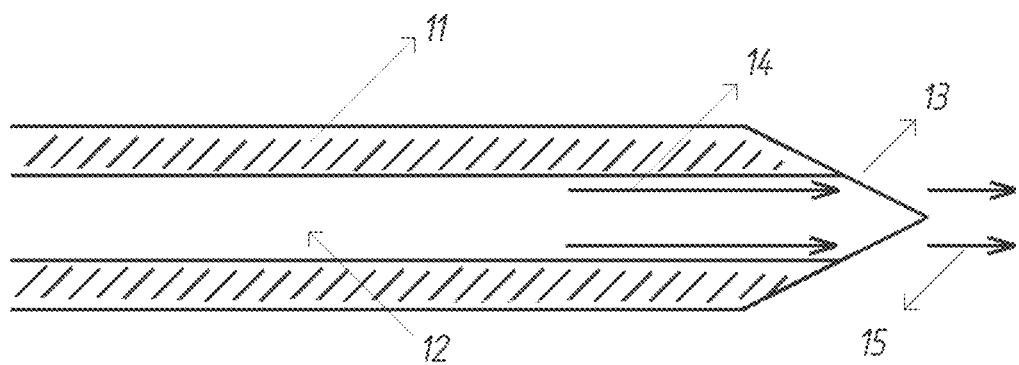
FIGS. 1a and 1b illustrate a preferred embodiment of the present invention in which the disclosed device comprises a glass optical fiber with a conical tip.

An optical waveguide (e.g. a glass optical fiber, a fiber bundle or a planar waveguide) is surrounded by a gaseous or a liquid or a solid state medium. The refractive indices of the waveguide materials and the surrounding medium are such that a significant fraction of the optical radiation, being transported in the waveguide, is coupled out of the waveguide in a peripheral surface area into the surrounding medium. If the optical radiation has an appropriate wavelength and sufficient power density, the surrounding medium will be changed in the vicinity of at least a part of the peripheral surface area. The peripheral surface area is the area of the waveguide where the optical radiation can exit the waveguide before the radiation altered the optical properties of the surrounding medium. The distal surface area is the area at the distal end of a waveguide and is the part of the waveguide from which optical radiation is emitted when the refractive index of the surrounding medium has changed.

Said optical radiation can originate from a laser, a LED, an array of LEDs, a halogen lamp or any other light source that provides appropriate wavelengths and power density levels to alter the optical properties of the surrounding medium, namely its refractive index, in the vicinity of the peripheral surface area of the waveguide.

The changes of the surrounding medium result in a change of its refractive index (typically a lowering of the refractive index) such that optical radiation, exiting the waveguide, is redirected. Vaporization of a liquid medium or liquefying of a solid state material or of some of its components might result in such changes of a surrounding medium.

Surrounding liquid media in medical environments can be e.g. blood, saline solution or any other aqueous or non-aqueous solution that is present during the medical intervention. In case of blood and aqueous solutions, wavelengths like e.g. 980 nm, 1470 nm or around 2 µm (including 1950 nm) are advantageous as they are well-absorbed by the water molecules which are contained in the liquid medium. A combination of wavelengths can be used where a first wavelength such as 1470 nm is used to partially evaporate surrounding aqueous solution to influence the emissions characteristics and a second wavelength such as 980 nm is used to coagulate or ablate biological tissue next to the fiber's distal end.

Surrounding solid state materials during medical treatments can be e.g. prostate tissue, muscular tissue, adipose tissue or vascular walls. Besides those kinds of tissues themselves, enclosed water, blood or fat cells can be the absorbing components. Therefore, optical wavelengths that are well absorbed by water molecules are advantageous as well for the modification of solid-state material.

In case of blood or blood containing tissue a wavelength in the green spectral region (e.g. 532 nm) might be advantageous, based on its high absorption in hemoglobin moieties, with respect to its feasibility to change the refractive index of the surrounding medium.

The following examples illustrate preferred embodiments of present invention.

EXAMPLE 1

Glass Optical Fiber with a Conical Fiber Tip

Figure 1B:
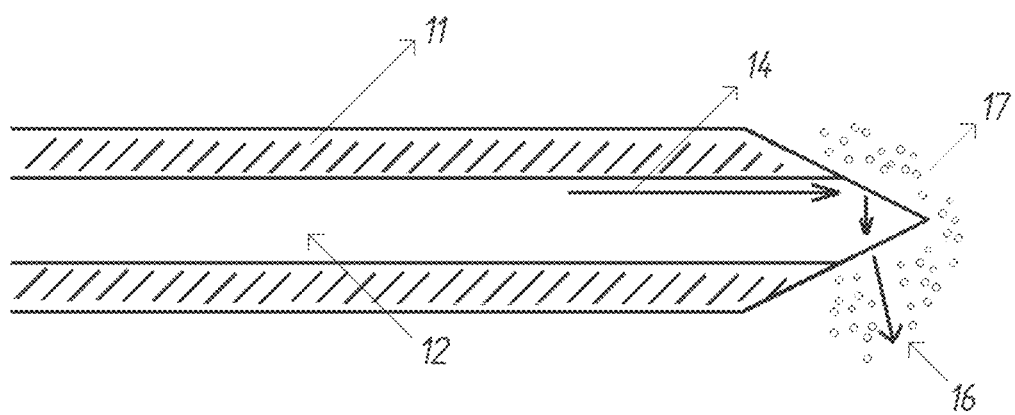

FIGS. 1a and 1b depict schematically a preferred embodiment which comprises a glass optical fiber with a fiber core (12) having a refractive index $n_1$ and a fiber clad (11) having a refractive index $n_2$ which is lower than $n_1$. The fiber distal tip (13) has a cone shape.

When such a probe is surrounded by an aqueous solution (e.g. inside a vein which is supplied with blood) a significant fraction of the optical radiation (14) that is transported inside the fiber core will be transmitted through the conical fiber tip and emitted in forward direction (15) as illustrated in FIG. 1a.

As depicted in FIG. 1b, the optical power, being emitted in forward direction, is absorbed by the surrounding liquid medium which is evaporated and thus forms steam bubbles (17) in the vicinity of the peripheral surface of the fiber's distal end, here conical fiber tip (13). As the refractive index of water vapor is significantly lower than the one of liquid water, the refractive index step between fiber material (11, 12) and surrounding medium (which is now a vapor) is significantly enlarged. Therefore, the emission characteristics of the optical probe are altered, i.e. most of the optical radiation is emitted in radial direction (16).

In another preferred embodiment, at least a part of optical power, being emitted in forward direction heats distal fiber tip (13). The heated waveguide, in turn, heats up the surrounding medium. Thus, the refractive index of the surrounding medium is altered indirectly in the vicinity of at least a part of the peripheral surface area. Therefore, the emission characteristics of the optical probe are altered such that a greater part of the optical radiation is emitted in radial direction (16).

EXAMPLE 2

Glass Optical Fiber with a Bent Fiber Tip

Figure 2A:
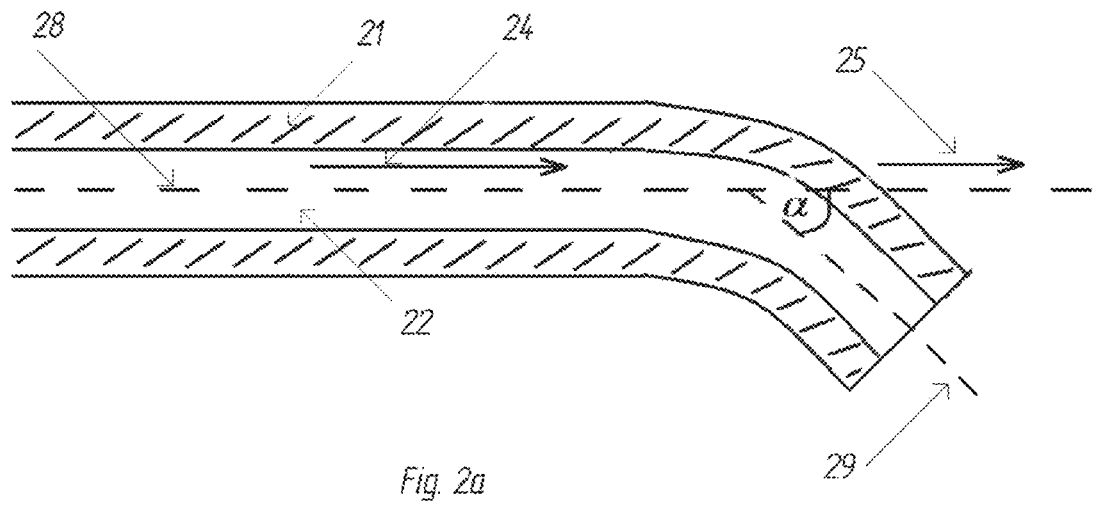
FIGS. 2a and 2b depict a preferred embodiment of the present invention in which the disclosed device comprises a glass optical fiber with a bent fiber tip.
Figure 2B:
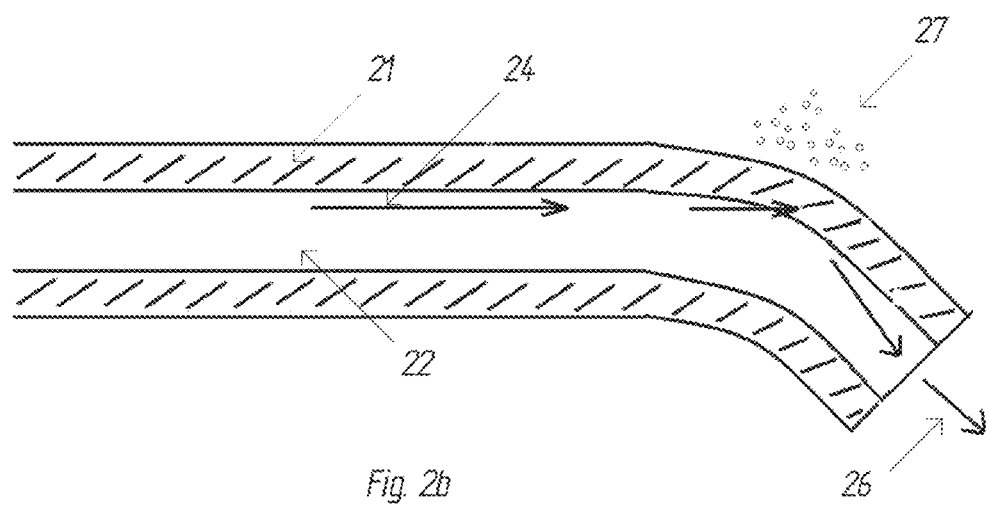

FIGS. 2a and 2b depict schematically a preferred embodiment which comprises a glass optical fiber with a fiber core (22) having a refractive index $n_1$ and a fiber clad (21) having a refractive index $n_2$ which is lower than $n_1$. The fiber tip is bent sideward off the long axis of the fiber axis. Fiber axis (28) and the normal (29) to the fiber's end facet enclose the angle α. Typical values of α are in the order of 20-35°.

FIG. 2a illustrates that a significant fraction of the optical power (25) is transmitted in forward direction.

EXAMPLE 3

Fiber with a Beveled Tip

Figure 3A:
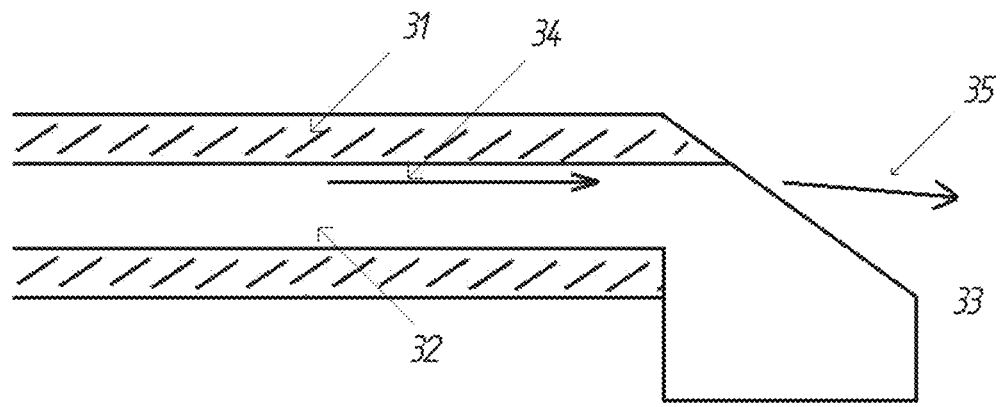
FIGS. 3a and 3b illustrate a preferred embodiment of the present invention in which the disclosed device comprises a glass optical fiber with a planar area of the surface to redirect the transmitted laser radiation.
Figure 3B:
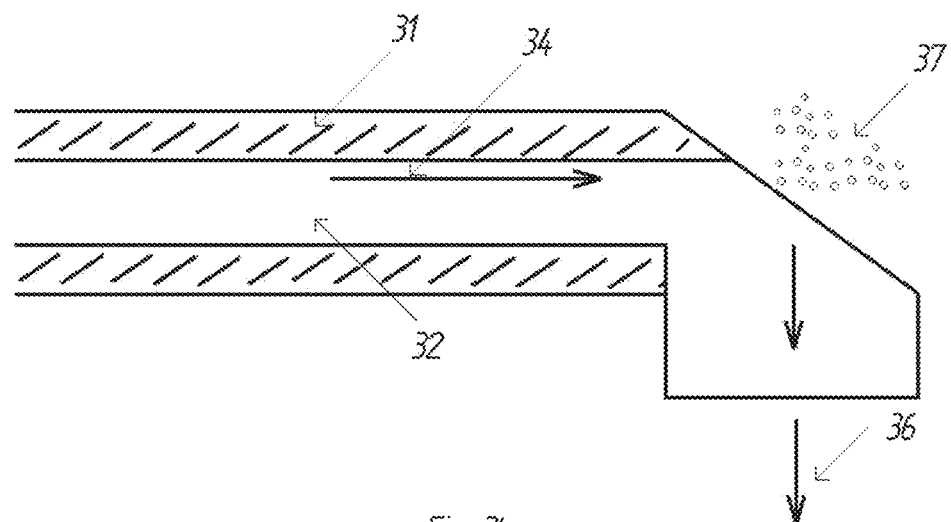

Another preferred embodiment is a fiber with a beveled fiber tip as shown in FIGS. 3a and 3b. Laser radiation (34) is transmitted through the fiber core (32) by means of total internal reflection at the core/clad boundary where the fiber's clad (31) has a refractive index $n_2$ lower than the core's refractive index ($n_1$).

As the refractive index of the surrounding aqueous solution is lower than $n_1$, but larger than the refractive index of air or even water vapor, laser light is emitted in frontal direction (35) through the beveled tip (33). Once laser radiation (35) has vaporized a certain amount of the aqueous solution and steam bubbles (37) occur, the refractive index step between the fiber core and its surrounding is changed. The refractive index of the vaporized aqueous solution (37) is low enough that near total reflection occurs at the core/vapor interface. Thus, laser radiation is directed sideways (36).

EXAMPLE 4

Glass Optical Fiber with a Fiber Tip where the Distal End of the Fiber is Protected by a Glass Sleeve A glass optical fiber, having a fiber core (42) surrounded by a fiber clad (41), is inserted into a protective sleeve (43) where the inner diameter of said sleeve is (slightly) larger than the outer diameter of the fiber clad (41). Thus, there is a gap (48) between the surface of the glass optical fiber and the inner walls of the protective sleeve (43). The proximal end of the protective sleeve (43) is connected (49) to the glass optical fiber either by fusion, splicing or gluing. Said gap (48) between fiber and sleeve remains unaffected in the vicinity of the fiber's distal end. Sleeve and fiber are bent in the vicinity of the distal end.

Liquid might enter said gap and thus could cause an output coupling of a fraction of the optical radiation (45). In case the optical radiation is absorbed by the liquid that fills the gap, said liquid is evaporated (47) and thus removed from the fiber's surface.

The resulting changes in refractive index of the material filling the gap yield altered emission characteristics (46) of the distal end of the fiber. The numerical aperture in the liquid phase can be higher than the NA of the waveguide itself.

Figure 4A:
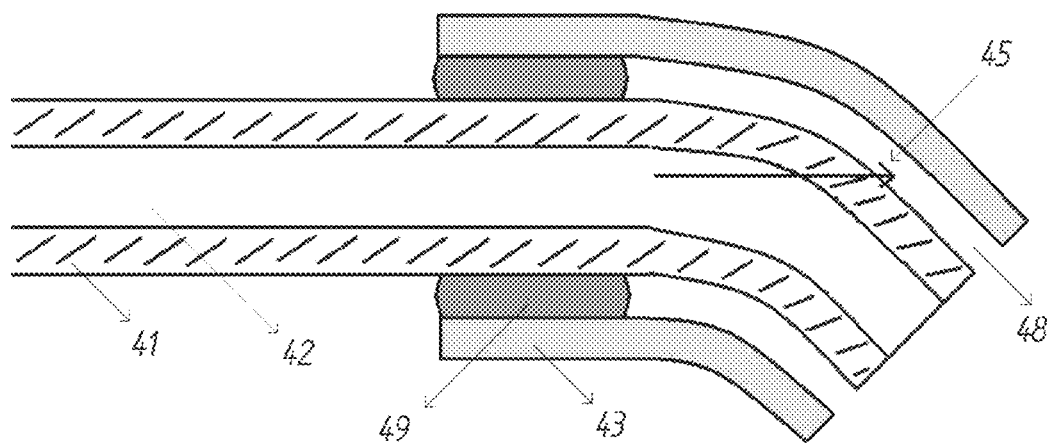
FIGS. 4a and 4b depict a preferred embodiment of the present invention in which the disclosed device comprises a glass optical fiber with glass sleeve. The sleeve is fused to the glass optical fiber at the proximal end of the sleeve. At the distal end of fiber and sleeve, there is a gap between the fiber's surface and the inner surface of the sleeve.
Figure 4B:
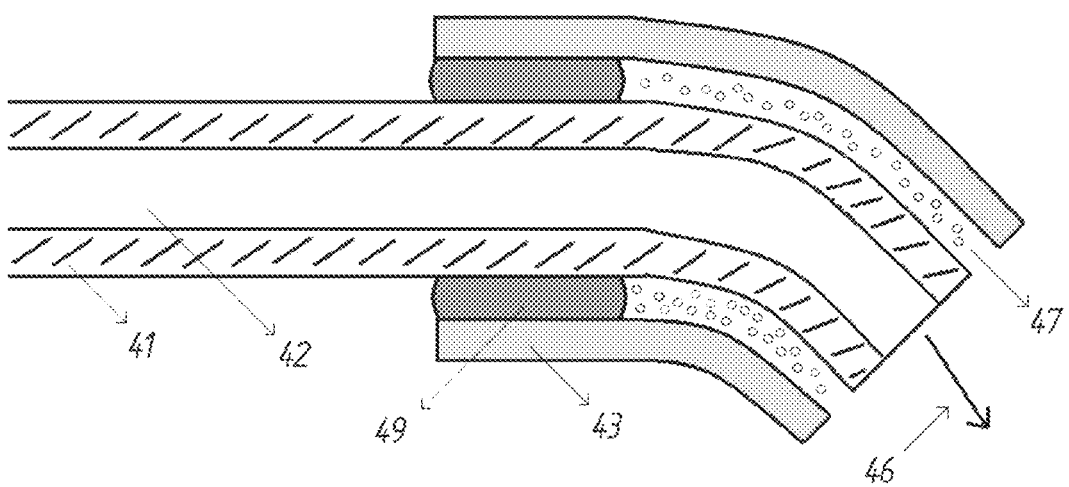

This preferred embodiment is illustrated in FIGS. 4a and 4b.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A device comprising an optical waveguide that transports optical radiation from its proximal end to its distal end and that is surrounded by a medium at least in the area of its distal end and where a certain fraction of light is at least initially emitted through said waveguide's peripheral surface area; and said certain fraction of light being configured such that said fraction of light changes the refractive index of said surrounding medium at least in the vicinity of said peripheral surface area, in such a way that radiation emitted from said waveguide is redirected;

wherein said optical waveguide is a glass optical fiber having a core with refractive index $n_1$ surrounded by a cladding with refractive index $n_2$ and where $n_1 > n_2$;

wherein the glass optical fiber is shaped at its distal end in such a way that a certain fraction of the transmitted optical radiation is coupled out of the fiber core and extracted in forward direction; said certain fraction of the transmitted optical radiation being configured such that a vapor bubble, caused by interaction of said surrounding medium with said certain fraction of the transmitted optical radiation, allows for the redirection of remaining optical radiation such that said remaining optical radiation is emitted laterally from a glass optical fiber's distal end facet; and wherein at least two laser wavelengths are transmitted through the device, and wherein at least one wavelength is well-absorbed by said surrounding medium and a second wavelength is used for a medical treatment.

2. The device according to claim 1 wherein the refractive index of said surrounding medium is lowered in the vicinity of the peripheral surface area of said waveguide after interaction with said fraction of light initially emitted through said surface area.

3. The device according to claim 1 wherein the surrounding medium is selected from a group consisting of a gas material, a solid material and a liquid material.

4. The device according to claim 3 wherein said surrounding solid material is biological tissue.

5. The device according to claim 4 wherein said biological tissue is selected from the group consisting of muscular tissue, adipose tissue, prostate tissue, vascular walls.

6. The device according to claim 1 wherein the surrounding medium is a liquid material which is vaporized by said fraction of light.

7. The device according to claim 1 wherein the glass optical fiber has a conical tip at its distal end.

8. The device according to claim 7 where a aqueous solution that surrounds the conical fiber tip is evaporated by a fraction of the laser radiation which is emitted from the fiber tip and forms a steam bubble surrounding said fiber tip, and wherein the remaining fraction of the laser radiation is emitted from the fiber tip in radial direction due to the fact that the refractive index of the steam is lower than the refractive index of the liquid aqueous solution.

9. The device according to claim 1 wherein the medium that surrounds the fiber tip is evaporated by a fraction of the laser radiation which is emitted from the fiber tip and forms a vapor bubble surrounding said fiber tip and wherein the remaining fraction of the laser radiation is emitted from the fiber tip in radial direction due to the fact that the refractive index of the vapor is lower than the refractive index of the liquid aqueous solution.

10. The device according to claim 1 where the distal end of said fiber is protected by a sleeve that is made from glass.

11. The device according to claim 10, wherein said sleeve is fused to said glass optical fiber at the proximal end of said sleeve.

12. The device according to claim 11, wherein a gap exists between said fiber's surface and the inner surface of said sleeve at the distal end of said sleeve.

13. The device according to claim 12, where said gap is filled with said medium and wherein said medium is removed from said gap by a certain fraction of optical radiation.

14. A device comprising an optical waveguide that transports optical radiation from its proximal end to its distal end and
that is surrounded by a medium at least in the area of its distal end and
where a certain fraction of light is at least initially emitted through said waveguide's peripheral surface area; and
said certain fraction of light being configured such that said fraction of light changes the refractive index of said surrounding medium at least in the vicinity of said peripheral surface area, in such a way that radiation emitted from said waveguide is redirected;
wherein said light is laser radiation with at least one wavelength that is well absorbed by said surrounding medium;
wherein at least two laser wavelengths are transmitted through the device, and wherein at least one wavelength is well-absorbed by said surrounding medium and a second wavelength is used for a medical treatment; and
wherein said at least one wavelength is used to partially evaporate surrounding aqueous solution to influence the emissions characteristics of said device and wherein a second wavelength is used to coagulate and/or ablate biological tissue next to the fiber's distal end either in contact or non-contact mode.

15. The device according to claim 14 wherein said surrounding medium is an aqueous solution and said at least one wavelength is preferably selected from the group of spectral regions 800-1100 nm, 1400-1600 nm and 1800-2100 nm.

16. The device according to claim 15 wherein said at least one wavelength is selected from the group consisting of about 980 nm, about 1470 nm and 1950 nm.

17. The device according to claim 15 wherein the aqueous solution that surrounds the conical fiber tip is evaporated by a fraction of the laser radiation which is emitted from the fiber tip and forms a steam bubble surrounding said fiber tip and wherein the remaining fraction of the laser radiation is emitted from the fiber tip in radial direction due to the fact that the refractive index of the steam is lower than the refractive index of the liquid aqueous solution.

18. The device according to claim 14 wherein said at least two laser wavelengths are preferably 980±40 nm and 1470±40 nm.

19. A method for medical treatments, the method comprising using the device according to claim 1 for medical treatments.

20. A method for treatment of benign prostate hyperplasia (BPH), the method comprising:
using the device according to claim 14 for the treatment of benign prostate hyperplasia (BPH), use of the device comprising:
partially evaporating, using the first wavelength, surrounding aqueous solution to influence the emissions characteristics of said device; and coagulating and/or ablating, using second wavelength, the biological tissue next to the fiber's distal end either in contact or non-contact mode.

21. A method for treatment in phlebology, including treatment of varicose veins by an endoluminar procedure, the method comprising:
using the device according to claim 14 for treatments in phlebology, the treatment of varicose veins by an endoluminar procedure, use of the device comprising:
partially evaporating, using the first wavelength, surrounding aqueous solution to influence the emissions characteristics of said device; and coagulating and/or ablating, using second wavelength, the biological tissue next to the fiber's distal end either in contact or non-contact mode.

* * * * *